United States Patent [19]

Long et al.

[11] 4,363,914

[45] Dec. 14, 1982

[54] PREPARATION OF BENZOTRIAZOLES

[75] Inventors: John W. Long, Cincinnati; Lubomir Vacek, Toledo, both of Ohio

[73] Assignee: The Sherwin-Williams Company, Cleveland, Ohio

[21] Appl. No.: 222,445

[22] Filed: Jan. 5, 1981

[51] Int. Cl.³ .................. C07D 249/18; C07D 249/20
[52] U.S. Cl. .................................... 548/257; 548/260; 548/261
[58] Field of Search ....................... 548/257, 260, 261

[56] References Cited
U.S. PATENT DOCUMENTS 3,970,667  7/1976  Gengnagel et al. ............. 260/308 B

OTHER PUBLICATIONS

Kitano, et al., "1,2,3 Benzotriazoles", Chem. Abst. 79:115594v.
Organic Synthesis, vol. 20, pp. 16-18 (1940).
Handbook of Chemistry and Physics, (1977) pp. C-155 and C-207.

Primary Examiner—Donald G. Daus
Assistant Examiner—G. Hendricks
Attorney, Agent, or Firm—Robert E. McDonald; James V. Tura

[57] ABSTRACT

This invention relates to a process for producing benzotriazoles which comprises effecting a mixture in an aqueous medium of at least one aromatic orthodiamine and one or more nitrites and heating the mixture to temperatures ranging up to about 350° C. while maintaining pressures at levels sufficient to keep effective amounts of water present for the reaction.

18 Claims, No Drawings

PREPARATION OF BENZOTRIAZOLES

BACKGROUND OF THE INVENTION

This invention relates to a novel process for the production of aromatic triazoles and their salts. More particularly, this invention relates to a process for producing aromatic triazoles which involves effecting a mixture of one or more nitrites and an aromatic orthodiamine in an aqueous medium under conditions of elevated temperatures and pressures.

SUMMARY OF THE PRIOR ART

Aromatic triazoles, especially benzotriazole and tolyltriazole, have found widespread application as corrosion inhibitors, chemical intermediates, photographic chemicals and catalysts.

Diazotization reactions involving aromatic amines and nitrous acid are known in the chemical arts. In addition, the reaction of orthodiamines with nitrous acid has been shown to produce benzotriazoles, as pointed out in U.S. Pat. No. 2,861,078. The prior art methods, however, typically require the addition of one equivalent of an acid reacting substance for each equivalent of nitrite in the aqueous mixture of nitrite and amine in order to generate nitrous acid as a reactant. This approach has several drawbacks. The added acids can cause the formation of highly colored by-products and tars by diazo coupling thereby decreasing the yield and the quantity of the product. This is especially true when the acid is a lower cost mineral acid rather than an organic acid. In order to minimize this problem at least some of the added acid is usually one of the more expensive organic acids thereby adding to the total cost of the product. Furthermore, the addition of the acid is a time consuming production step which also adds to the total cost of the product. Also, in order to minimize the production of nitrous oxide pollutants, it is essential to obtain the fastest possible dispersion of the added acid in the reaction vehicle. Because this is very difficult, pollution control equipment must be used. Furthermore, under the prior art process, if the water soluble alkali metal salt of the aromatic triazole is the desired final product, caustic must be added after the reaction is completed to convert the free triazole to its alkali metal salt. The method of this invention, however, involves effecting a mixture in an aqueous medium of at least one aromatic orthodiamine and one or more nitrites and maintaining or reacting said mixture at temperatures ranging up to about 350° C. at an effective pressure. By this method, there is no need for the addition of an equivalent amount of an acid reacting substance into the reaction and the expense, handling problems and side reactions caused by the acid can be avoided.

BRIEF SUMMARY OF THE INVENTION

It is an object of this invention to provide an improved process for the preparation of benzotriazoles. Another object of this invention is to provide a process for the preparation of benzotriazoles which involves maintaining the reaction at temperatures ranging up to about 350° C. and at pressure higher than atmospheric pressure. Another object of this invention is to provide a process for the preparation of benzotriazoles from aromatic orthodiamines which avoids the cost and handling problems involved in the use of equivalent amounts of acids during the reaction. These and other objects of the invention will become apparent from the description and examples which follow.

This invention involves a process for producing aqueous salts of benzotriazoles which comprises mixing in the presence of water reactive amounts of (a) at least one aromatic orthodiamine and (b) at least one metal nitrite, by heating the aqueous mixture at temperatures ranging up to about 350° C. and at pressures sufficient to maintain liquid water in the reaction. For purposes of this disclosure, reactive amounts means essentially equimolar ratios of diamine to nitrite and in particular between about 0.95 and 1.1 moles of nitrite for each mole of diamine. Especially preferred is a level of about 1.00 to 1.05 moles of nitrite for each mole of diamine.

When the desired product is the free triazole, rather than the water soluble salt, the free triazole can be readily generated by the addition of a sufficient amount of acid to neutralize the basic salt. Typically a pH of less than 7 and especially less than about 6 is sufficient to generate the free triazole. It is preferred to use the less expensive mineral acids, especially sulfuric acid, to generate the free triazole. Once the pH has been adjusted to the acidic side, the free triazole can be separated by decantation or by a separatory funnel or other methods known in the art.

DETAILED DESCRIPTION OF THE INVENTION

Benzotriazoles are typically commercially available in two forms, either as the pure (free) benzotriazoles or as aqueous solutions of their soluble salts, such as the sodium salts. The process described herein works very well for the production of either commercial form, however, it is most especially suited for the preparation of the aqueous sodium salt solution because that product can be used directly upon its removal from the reactor and requires no further processing or purification. In addition, with the selection of proper reaction equipment which would allow rapid heating to the proper reaction temperatures, this process can be conveniently used as a continuous process for the production of benzotriazoles.

When free benzotriazole is the desired product, the reaction mixture can be conveniently worked up by acidifying the crude mixture to a pH of about 6 or less, separating the benzotriazole oil from the water and then, if desired, purifying the recovered oil by any of the methods well known within the art, such as recrystalization.

The aromatic orthodiamines which are useful in the practice of this invention have the following structure:

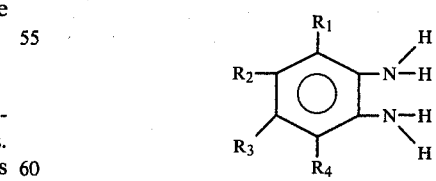

wherein $R_1$, $R_2$, $R_3$, and $R_4$ can be the same or different and are selected from the group consisting of hydrogen, alkyl, alkoxy, aryl, aroxy, aralkyl, aralkoxy, alkaroxy, halogen, and nitro, and wherein two or more of the $R_1$, $R_2$, $R_3$, and $R_4$ groups could be part of a fused ring structure. Examples of such known diamines include 1,2-benzenediamine, 3-methyl-1,2-benzenediamine, 4- methyl-1,2-benzenediamine, 4-nitro-1,2-benzenediamine, carboethoxy-1,2-benzenediamine, 1,2-naphthalenediamine, 4-bromo-1,2-naphthalenediamine, and the orthodiaminoanthroquinones. The preferred starting materials are 1,2-benzenediamine and the 3- or 4-methyl-1,2-benzenediamines because these produce benzotriazole and methylbenzotriazoles (tolyltriazoles) which are the aromatic triazoles of the greatest current commercial interest.

In those instances when it is preferred to have triazole products with the lightest color possible, it may be preferred to purify the commercial diamine product prior to its use in the reaction. This typically can be accomplished by distillation which removes the high boiling color bodies, or if the color needs to be minimized even more, the diamine may be fractionated as is well known in the art, to remove both the high boiling color bodies and the low boiling toluidines and other impurities which also impart color. This purification step is especially useful if the triazole product is to be sold without further purification after its manufacture. Even lighter colored distillates can be obtained by adding about 0.1% by weight of sodium borohydride to the diamine before the distillation or fractionation.

In general, any metal nitrite can be employed in the production of triazoles according to the process of this invention. Especially preferred are the alkali metal nitrites because of their high water solubility, availability and relatively low cost. Sodium nitrite is especially preferred for use in the practice of this invention.

As previously mentioned between about 0.95 and 1.1 moles of nitrite should be used for each mole of diamine. However, in order to drive the reaction to completion, it is preferred that at least about one mole of nitrite be used for each mole of the aromatic diamine and it is especially preferred to use the nitrite in about a 5 to 10% excess over equimolar proportions. The reaction taught in this invention must be maintained at temperatures which are higher than those of a typical diazotization reaction. The reaction in accordance with this process can be conducted at temperatures ranging up to about 350° C. although the preferred range for the reaction is between about 100° C. and 350° C. and especially preferred is between about 200° C. and 300° C.

If desired, the reaction of the aromatic orthodiamine and the nitrite can be conducted in the presence of a catalytic amount of an acid. Useful levels of catalyst typically range from about 0.1% to about 2% by weight of the aromatic orthodiamine used in the reaction. Especially preferred is a level of catalyst at about 1% of the weight of the aromatic orthodiamine. Organic materials having a $K_a$ between about $10^{-5}$ and $10^{-9}$ are the preferred acid catalysts. Especially preferred as catalysts are triazoles themselves. Their presence in the reaction products at the end of the reaction has no adverse effects because in that case the catalysts are the same chemical species as the eventual product of the reaction.

In order to insure complete reaction of the amine and the nitrite, there must be enough water present in the system to provide for solubility of the reactants. For ease of handling, it is generally preferred to use between about 1.5 to 3.5 parts by weight of water for each part by weight of the nitrite, but greater or lesser amounts of water are also effective. Since at least enough liquid water to provide solubility for the reactants is essential for this reaction and since the reaction temperatures are often above the normal boiling point of water, it is essential to maintain pressure above atmospheric pressure within the reaction vessel during the course of this reaction. The pressure must be sufficiently high enough to prevent the vaporization of so much of the water available that solubility of the reactants can no longer be maintained. These pressures can be conveniently maintained by using a closed reaction vessel which can withstand high internal pressures and by adding sufficient quantities of the reactants so that the free volume within the reaction chamber is so limited that as water is vaporized, it increases the pressure within the reaction chamber to such a level that liquid water can be maintained in equilibrium with the vapor phase. Under typical reaction conditions for this invention the pressure inside the reaction vessel would be above about 70 pounds per square inch (psi) and would typically be between about 70 psi and 1000 psi depending upon the reaction temperature, the size of the reaction vessel, and the amount of free volume within the reaction chamber.

DESCRIPTION OF THE PREFERRED EMBODIMENTS

The following examples have been selected to illustrate specific embodiments and practices of advantage to a more complete understanding of the invention. Unless otherwise indicated all % figures are weight percent.

EXAMPLE 1

Stainless steel reactors (⅜ inch pipe end caps fitted with plugs) were charged with 0.1 gram of 1,2-benzenediamine and 0.2 milliliters of 37% aqueous sodium nitrite and were sealed and placed in a constant temperature bath. Reactors were withdrawn from the constant temperature bath one at a time and immediately cooled by immersion in an ice bath. The cooled reactors were opened and the contents were analyzed by high performance liquid chromatography for benzotriazole content. The results are outlined in Table I.

TABLE I

| HIGH TEMPERATURE DIAZOTIZATION OF 1,2-BENZENEDIAMINE TO BENZOTRIAZOLE | | |
|---|---|---|
| Reaction Time (minutes) | % Conversion to benzotriazole at 250° C. | % Conversion to benzotriazole at 300° C. |
| 5 | 21 | 79 |
| 10 | 43 | 96 |
| 15 | 52 | 98 |
| 20 | 61 | 100 |

EXAMPLE 2

In a manner similar to Example 1, 0.1 grams of orthotoluenediamine (mixture of the 3-methyl-1,2 benzenediamine and 4-methyl-1,2-benzenediamine) and 0.2 milliliters of 37% aqueous sodium nitrite were charged into stainless steel reactors which were sealed and placed in a constant temperature bath. Reactors were withdrawn from the constant temperature bath one at a time and immediately cooled by immersion in an ice bath. The contents of the cooled reactors were analyzed by high performance liquid chromatography for tolyltriazole (mixture of 4-methyl- and 5-methyl-1,2,3-benzotriazole) content. The results are outlined in Table II below.

TABLE II
HIGH TEMPERATURE DIAZOTIZATION OF ORTHOTOLUENEDIAMINE TO TOLYLTRIAZOLE

| Reaction Time (minutes) | % Conversion to Tolyltriazole at 266–270° C. | % Conversion to Tolyltriazole at 300° C. | % Conversion to Tolyltriazole at 328–330° C.* |
| --- | --- | --- | --- |
| 5 | 29 | 64 | 81 |
| 10 | 57 | 85 | 84 |
| 15 | — | 95 | 85 |
| 20 | 94 | 96 | 86 |
| 40 | 97 | — | — |

*10, 15, 20 minute samples from the 328–330° C. reaction temperature were under pressure when opened indicating decomposition of triazoles was taking place.

EXAMPLE 3

Into a two-liter autoclave fitted with a magnadrive stirrer, cooling coils, sampling valve, pressure gauge, rupture disc and heating mantle was charged 531.4 grams (4.92 moles) of 1,2-benzenediamine and 1010.0 grams of a 37% aqueous solution of sodium nitrite (5.42 moles $NaNO_2$). The autoclave was gradually heated to 260° C. over a period of about two hours. The autoclave was maintained at 260° C. and the corresponding pressure of between 430 and 480 psi for 3 hours with vigorous stirring and then cooled to about 50° C. by passing water through the cooling coils.

In order to work up the reaction product to obtain the free benzotriazole (rather than the sodium salt) the solution was made acidic by diluting the reaction product with an equal volume of water and adding 286 grams of concentrated sulfuric acid which reduced the pH from 11.7 to about 6.0. Upon acidification, the reaction product separated into two layers. The oil layer was separated, heated to a temperature of 100°–125° C. and dried under reduced pressure by use of a water aspirator. After purification, potentiometric analysis indicated the product was essentially 100% pure benzotriazole. The overall yield of benzotriazole was 96.9% of the theoretical.

EXAMPLE 4

A two-liter autoclave equipped as described in Example 3 was charged with 603 grams (approximately 4.94 moles) of distilled orthotoluenediamine and 918 grams of a 37% aqueous solution of sodium nitrite (approximately 4.92 moles of sodium nitrite) and 6.0 grams of tolyltriazole as catalyst. The reactants were gradually heated to 260° C. (which gave a pressure of about 300 psi) over a 65 minute period. The reaction was held at 260° C. and approximately 300 psi for about 70 minutes and then cooled. Analysis of the reaction materials by liquid chromatography indicated that some unreacted orthotoluenediamine was still present. Therefore, an additional 17.0 grams (approximately 0.09 mole sodium nitrite) of the 37% aqueous sodium nitrite solution was added to the autoclave to drive the reaction to completion. The reactants were reheated to 260° C. and held at that temperature and at about 320 psi pressure for an additional one hour period, then cooled by passing water through the cooling coils.

In order to work up the reaction mixture, the cooled contents of the autoclave were divided into two parts and each part was extracted two times with 150 milliliters of chloroform. The aqueous layers, which contain the sodium salts of the triazoles, were recombined and the free tolyltriazole regenerated from the salt from by adjusting the pH to about 5.8 by the addition of 64.7 grams of concentrated sulfuric acid. After removal of the water and purification of the product, the overall yield of tolytriazole was about 89.4% of the theoretical yield.

EXAMPLE 5

A two-liter autoclave equipped as described in Example 3 was charged with 603 grams (4.94 moles) of distilled orthotoluenediamine and 1010 grams of a 37% aqueous solution of sodium nitrite (approximately 5.42 moles of sodium nitrite). The reactants were heated to 260° C. over a period of about 90 minutes. The reaction was held at 260° C. and between 400 and 430 psi for about 2½ hours and then cooled. The cooled contents were extracted with chloroform and the aqueous layer was acidified by the addition of 267 grams of concentrated sulfuric acid to give a pH of about 6.0. The triazole oil was dried under reduced pressure. The overall yield of triazole, dry oil plus small amount retained in aqueous layer, was 98.4% of the theoretical yield.

EXAMPLE 6

A two-liter autoclave equipped as described in Example 3 was charged with 305 grams (2.5 moles) of freshly distilled orthotoluenediamine, 512.8 grams of a 37% aqueous solution of sodium nitrite (2.75 moles $NaNO_2$, 18 moles water) and 0.3 gram of sodium borohydride under a blanket of nitrogen gas. The reactants were heated to about 300° C. over a time period of about one hour and maintained at 300° C. and about 850 psi for two hours and then allowed to cool. Analysis indicated the product was approximately 50% solution of sodium tolyltriazole in water. The product had a Gardner color of about 18–19.

EXAMPLE 7

A sample of commercially available orthotoluenediamine was fractionated by using a fractionation column and distilling at about 100° C. and a pressure reduced to about 1 mm of mercury.

A 35% solution of $NaNO_2$ was prepared by mixing 174.2 grams (2.525 moles) of $NaNO_2$ with 324 grams of water. This solution and 305 grams (2.5 moles) of the fractionated orthotoluenediamine, 20.5 grams (0.154 mole) of tolyltriazole as catalyst and 0.3 gram sodium borohydride were charged under a blanket of $CO_2$ and $N_2$ gasses into a two-liter autoclave. The autoclave was equipped as shown in Example 3. The reactants were heated to 225° C. over a one hour period and then maintained at 225° C. and about 200 psi pressure for a total of about 4 hours until liquid chromatography analysis indicated the level of orthotoluenediamine remaining unreacted was less than 0.004%. After the product was removed from the autoclave, 6.2 grams (0.155 mole) of sodium hydroxide was added to insure that all of the tolyltriazole was in the form of the sodium salt. Analysis indicated the product of this example was an approximately 50% solution of sodium tolyltriazole in water with a Gardner color of 12–13.

EXAMPLE 8

The process described in Example 7 was repeated exactly except the sodium borohydride was not added. This reaction produced a product virtually identical in yield and color to that of Example 7.

Since it appears the sodium borohydride does not appreciably improve the color of the final product when merely added in with the reactants and since there is the possibility it would react with some of the sodium nitrite, the generally preferred method for practicing this invention does not involve an addition of sodium borohydride to the reaction mixture.

The foregoing examples, while illustrative, are not exhaustive. While this invention has been described by a number of specific embodiments, it is obvious that other variations and modifications can be made without departing from the spirit and scope of the invention as set forth in the appended claims.

The invention claimed is:

1. A process for producing aqueous metal salts of benzotriazoles consisting essentially of mixing in the presence of water reactive amounts of:
   (a) at least one aromatic orthodiamine having the structure:

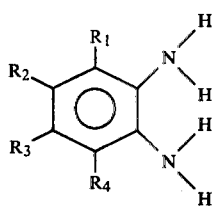

wherein $R_1$, $R_2$, $R_3$ and $R_4$ are the same or different and selected from the group consisting of hydrogen, alkyl, alkoxy, aryl, aroxy, aralkyl, aralkoxy, alkaroxy, and halogen wherein aryl and "ar-" is defined as phenyl and wherein alkyl or "alk-" is defined as having 1–50 carbons; and
   (b) at least one alkali metal nitrite; and heating the aqueous mixture at temperatures ranging from about 100° C. up to about 350° C. and at pressures sufficient to maintain liquid water in the reaction.

2. The process of claim 1 further characterized in that the pressures are maintained at levels sufficient to have enough liquid water to solubilize the diamine and nitrite.

3. The process of claim 1 further characterized in that the aromatic orthodiamine is 1,2-benzenediamine.

4. The process of claim 1 further characterized in that the aromatic orthodiamine is orthotoluenediamine.

5. The process of claim 1 wherein the alkali metal nitrite is sodium nitrite.

6. The process of claim 1 further characterized in that at least one mole of nitrite is present for each mole of aromatic orthodiamine.

7. The process of claim 6 further characterized in that between about 1.05 and 1.1 moles of nitrite are present for each mole of aromatic orthodiamine.

8. The process of claim 1 further characterized in that the pressure ranges above about 70 psi during the reaction.

9. The process of claim 8 further characterized in that the pressure is between about 70 psi and 1000 psi during the reaction.

10. The process of claim 1 further characterized in that the reaction temperature is between about 200° C. and 300° C.

11. The process of claim 1 further characterized in that the reaction takes place in the presence of a catalytic amount of an acid.

12. The process of claim 11 further characterized in that said acid is an organic material having a $K_a$ between $10^{-5}$ and $10^9$.

13. The process of claim 12 further characterized in that the organic material is a triazole.

14. The process of claim 1 further characterized in that the aromatic orthodiamine was purified by distillation or fractionation.

15. The process of claim 14 further characterized in that the aromatic orthodiamine was distilled or fractionated in the presence of sodium borohydride.

16. A process for producing benzotriazoles consisting essentially of:
   (a) preparing an aqueous solution of a metal salt of benzotriazoles by mixing in the presence of water reactive amounts of:
      (i) at least one aromatic orthodiamine having the structure:

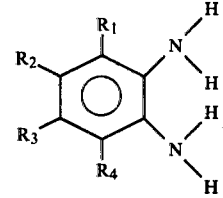

wherein $R_1$, $R_2$, $R_3$ and $R_4$ are the same or different and selected from the group consisting of hydrogen, alkyl, alkoxy, aryl, aroxy, aralkyl, aralkoxy, alkaroxy, and halogen wherein aryl and "ar" is defined as phenyl and wherein alkyl or "alk." is defined as having 1–50 carbons; and
      (ii) at least one alkali metal nitrite; and heating the aqueous mixture at temperatures ranging from about 100° C. up to about 350° C. and at pressure sufficient to maintain liquid water in the reaction; and
   (b) adding acid to the aqueous solution of salts of benzotriazoles to lower the pH below 7 to produce free benzotriazoles; and
   (c) separating the free benzotriazole from the aqueous solution.

17. A process for producing aqueous metal salts of benzotriazoles which comprises mixing in the presence of water reactive amounts of:
   (a) at least one aromatic orthodiamine selected from the group consisting of 1,2-benzenediamine, 3-methyl-1,2-benzenediamine, and 4-methyl-1,2-benzenediamine; and
   (b) at least one alkali metal nitrite; and heating the aqueous mixture at temperatures ranging from about 100° C. up to about 350° C. and at pressures sufficient to maintain liquid water in the reaction.

18. A process for producing benzotriazoles which comprises:
   (a) preparing an aqueous solution of a metal salt of benzotriazoles by mixing in the presence of water reactive amounts of: (i) at least one aromatic orthodiamine selected from the group consisting of 1,2-benzenediamine, 3-methyl-1,2-benzenediamine, and 4-methyl-1,2-benzenediamine; and (ii) at least one alkali metal nitrite; and heating the aqueous mixture at temperatures ranging from about 100° C. up to about 350° C. and at pressures sufficient to maintain liquid water in the reaction; and
   (b) adding acid to the aqueous solution of salts of benzotriazoles to lower the pH below 7 to produce free benzotriazoles; and
   (c) separating the free benzotriazole from the aqueous solution.

* * * * *